(12) United States Patent
Zheng et al.

(10) Patent No.: US 9,275,190 B2
(45) Date of Patent: Mar. 1, 2016

(54) METHOD AND SYSTEM FOR GENERATING A FOUR-CHAMBER HEART MODEL

(75) Inventors: Yefeng Zheng, Plainsboro, NJ (US);
Adrian Barbu, Tallahassee, FL (US);
Bogdan Georgescu, Plainsboro, NJ (US); Michael Lynch, Nuremberg (DE);
Michael Scheuering, Nürnberg (DE);
Dorin Comaniciu, Princeton Junction, NJ (US)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 2457 days.

(21) Appl. No.: 12/082,143

(22) Filed: Apr. 9, 2008

(65) Prior Publication Data
US 2008/0262814 A1 Oct. 23, 2008

Related U.S. Application Data

(60) Provisional application No. 60/913,343, filed on Apr. 23, 2007.

(51) Int. Cl.
*G06F 19/00* (2011.01)

(52) U.S. Cl.
CPC ............ *G06F 19/3437* (2013.01); *G06F 19/34* (2013.01); *G06T 2207/30048* (2013.01)

(58) Field of Classification Search
CPC .................. G06T 7/0012; G06T 2207/30048; G06T 7/0081; G06T 2207/30004; G06T 7/0087; G06T 7/0014; G06T 17/00; G06T 2207/20076; G06T 7/0028; G06T 7/2046; G06T 7/401

USPC .......................................... 345/420; 382/173
See application file for complete search history.

(56) References Cited

U.S. PATENT DOCUMENTS

| 5,889,524 | A | 3/1999 | Sheehan et al. | |
|---|---|---|---|---|
| 6,106,466 | A | 8/2000 | Sheehan et al. | |
| 6,873,718 | B2 | 3/2005 | O'Donnell et al. | |
| 2002/0172407 | A1* | 11/2002 | O'Donnell et al. | 382/131 |
| 2008/0304744 | A1* | 12/2008 | Peters et al. | 382/173 |
| 2009/0156933 | A1* | 6/2009 | Gerard et al. | 600/443 |

OTHER PUBLICATIONS

R.H. Davies, et al., "A Minimum Description Length Approach to Statistical Shape Modeling", IEEE Transactions on Medical Imaging, 21(5): pp. 525-537, 2002.
E. Praun, et al., "Consistent Mesh Parameterizations", In Proceedings SIGGRAPH, pp. 179-184, 2001.

* cited by examiner

*Primary Examiner* — Jeffrey Chow

(57) ABSTRACT

A method and system for building a statistical four-chamber heart model from 3D volumes is disclosed. In order to generate the four-chamber heart model, each chamber is modeled using an open mesh, with holes at the valves. Based on the image data in one or more 3D volumes, meshes are generated and edited for the left ventricle (LV), left atrium (LA), right ventricle (RV), and right atrium (RA). Resampling to enforce point correspondence is performed during mesh editing. Important anatomic landmarks in the heart are explicitly represented in the four-chamber heart model of the present invention.

25 Claims, 18 Drawing Sheets

METHOD AND SYSTEM FOR GENERATING A FOUR-CHAMBER HEART MODEL

This application claims the benefit of U.S. Provisional Application No. 60/913,343, filed Apr. 23, 2007, the disclosure of which is herein incorporated by reference.

BACKGROUND OF THE INVENTION

The present invention relates to modeling the heart in medical images, and more particularly, to modeling the heart by automatically generating a statistical four-chamber heart model from 3D volumes.

Various 3D shape representation techniques are used to model the heart. One type of heart model is a volume-based heart model. Tetrahedrons are often used to represent a solid volume model. Such volume-based models are widely used in finite element based approaches to study the blood flow of a heart. Volume-based models are also commonly used in active appearance models (AAM), since an AAM models the appearance inside an object. A tetrahedral mesh (model) can be generated automatically from labeled volume data.

Another type of heart model is a surface-based heart model. Using surface-based representation, only the shape boundary of an object is modeled. Accordingly, no information about the region inside the object is contained in a surface-based model. There are many ways to represent a surface, such as a triangulated mesh, a simplex mesh (which is a dual of the triangulated mesh in topology), and a B-spline mesh (which is parametric). How to generate a good surface mesh (using as few vertices as possible to meet a predefined error tolerance) from volume data is a widely researched topic in computer graphics.

In 3D heart segmentation, surface representations are widely used in snake-based deformable models or active shape models (ASM). Deformable models are not learning based and little shape priori information is used. Snake-based approaches do not need point correspondence, so they have more freedom to evolve a shape. For example, during the shape evolution, dynamically re-meshing can be used to produce high-quality meshes. However, it is impossible for dynamic re-meshing to be used for a statistic shape-based approach, such as ASM, since the predefined topology (for example, the number of mesh points and the connection among the mesh points) cannot be changed.

FIGS. 1 and 2 show conventional surface-based heart models. FIG. 1 shows a heart model built by New York University, freely available at http://education.med.nyu.edu/courses/old/embryology/courseware/vheart/. As illustrated in FIG. 1, image 102 shows the whole heart, image 104 shows the left ventricle (LV), image 106 shows the left atrium (LA), image 108 shows the right ventricle (RV), and image 110 shows the right atrium (RA). The model of FIG. 1 is not accurate in anatomy. For example, the shape of the short axis of intersection of the RV is a crescent with two cusp points. The mesh (model) should have a sharp turn at each of the cusp points, but the model of FIG. 1 rounds these cusps. FIG. 2 shows a heart model commercially available from Zygote Media Group, Inc. at http://www.3dscience.com/3D_Models/Human_Anatomy/Heart/index.php. As illustrated in FIG. 2, image 202 shows the whole heart, image 204 shows the LV, image 206 shows the LA, image 208 shows the RV, and image 210 shows the RA. The model of FIG. 2 is built from real CT and MRI volumes, so it is more accurate in anatomy than the model of FIG. 1. However, a drawback of the model of FIG. 2 is that it is too detailed, and may contain irrelevant details for many tasks. Another drawback of the model of FIG. 2 is that the LV epicardial border is not modeled. Instead, the pericardial border of the whole heart is represented.

Another type of heart model is a statistical shape model. In order to build a statistical shape model from a group of shapes, each shape must have the same number of points and the points should have correspondence. Point correspondence refers to point i in shape A and point i in shape B corresponding to the same anatomical structure. For example, if the $99^{th}$ point in shape A is the LV apex, the $99^{th}$ point in shape B should correspond to the LV apex, as well. Pair-wise based approaches for establishing point correspondence are easy and fast. In such pair-wise based approaches, one shape is selected and all other shapes are matched (registered) to the selected shape. After this registration, the average of the aligned shapes is used as the mean shape. This process can be iterated to refine the mean shape. A surface mesh is then generated from the mean shape, and the surface mesh is warped toward each individual shape. Using this approach, pseudo-landmarks are sampled in a consistent way for all training shapes. In R. H. Davies, et al., "A Minimum Description Length Approach to Statistical Shape Modeling", *IEEE Trans. Medical Imaging*, 21(5):525-537, 2002, a group-wise based method is proposed, in which the selection of pseudo-landmarks is formulated as an optimization problem to minimize the Minimum Description Length (MDL). A problem with this approach is that, if a dense representation is desired, the number of variables (the positions of pseudo-landmarks on each training shape) for optimization is very large. Accordingly, the optimization process is very slow and likely to converge to a local optimum.

Another approach for establishing point correspondence is to establish correspondence among shapes during the manual labeling process. This approach is relatively easy for 2D curves. Typically, only a few landmarks need to be labeled, such as points with high curvature. Uniform sampling between two neighboring landmarks on the curve will result in a dense point representation. However, it is difficult to manually label the correspondence in 3D because many more points are involved and there is no natural ordering of mesh points. In Praun et al., "Consistent Mesh Parameterizations", In *Proc. SIGGRAPH*, pages 179-184, 2001, a few sparse landmarks are labeled on 3D data. Assuming that the topology (i.e., the connection between landmarks) is given, they propose a method to fit this coarse mesh to the data is a consistent way by minimizing an energy function. Since the energy function is non-linear containing multiple local optima, many heuristics are proposed to search for a good local optimum solution. However, the algorithm proposed by Praun et al., is quite complicated and the optimization step is slow.

BRIEF SUMMARY OF THE INVENTION

The present invention provides a method for generating a four-chamber statistical heart model based on image data in 3D volumes. The model explicitly models important anatomic landmarks in the heart. Embodiments of the present invention can be utilized to generate a model based on a single 3D volume or based on a dynamic 3D volume sequence.

In one embodiment of the present invention, a 3D volume, such as a CT volume, ultrasound volume, etc., is received. A left ventricle (LV) mesh and a left atrium (LA) mesh are generated based on the 3D volume. The LV mesh and the LA mesh can be generated by editing or deforming an initial LV mesh and an initial LA mesh based on landmarks such as the mitral valve and the aortic valve. A right ventricle (RV) mesh and a right atrium (RA) mesh are generated based on the 3D volume. The RV mesh and the RA mesh can be generated by editing or deforming an initial RV mesh and an initial RA mesh based on landmarks such as a U-plane dividing the RV into three portions, the tricuspid valve, and the pulmonary valve. The LV, LA, RV, and RA meshes are resampled to establish mesh point correspondence. The resampling of the meshes occurs during mesh editing. The LV, LA, and RA meshes can be resampled using rotation axis based resampling, and the RV can be resampled using slice based resampling. The LV, LA, RV, and RA meshes are then used to generate a statistical heart model.

These and other advantages of the invention will be apparent to those of ordinary skill in the art by reference to the following detailed description and the accompanying drawings.

DETAILED DESCRIPTION

Figure 1:
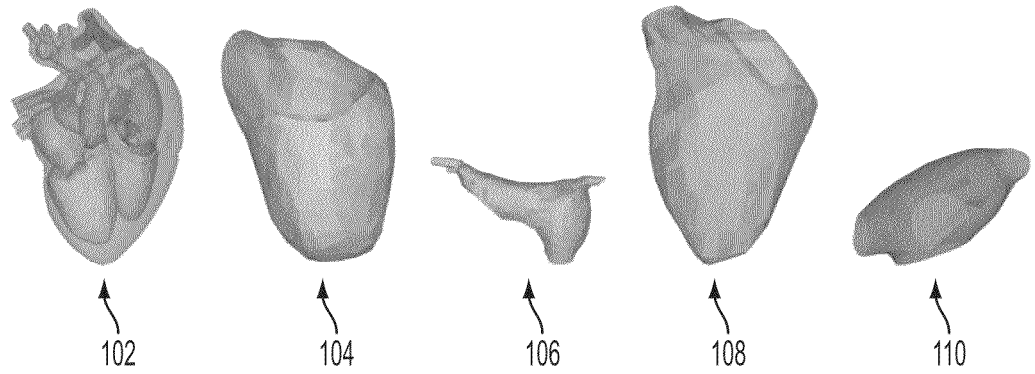
FIGS. 1 and 2 illustrate conventional surface-based heart models.
Figure 2:
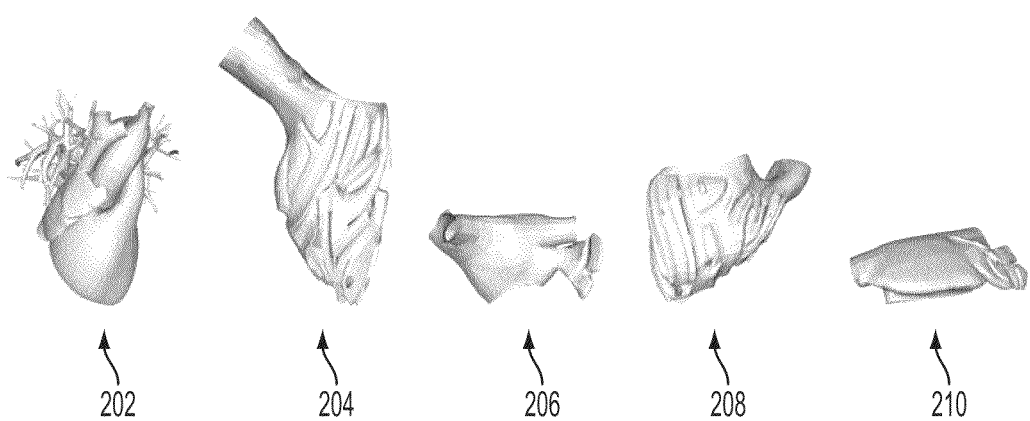

The present invention is directed to a method for generating a statistical four-chamber heart model from dynamic 3D volume sequences, such as CT volumes, ultrasound, etc. Embodiments of the present invention are described herein to give a visual understanding of the heart modeling method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Three-dimensional (3D) shape representation is typically more difficult than two-dimensional (2D) shape representation. Since it is hard to visualize 3D information, manipulation of 3D shapes can be very difficult. In most cases, it is necessary to visualize and manipulate 2D slices of 3D shapes. Also, there is no natural built-in ordering for landmarks on a 3D mesh. Since landmarks are sparse, pseudo-landmarks are typically interpolated to get a dense representation in order to build an accurate shape model. In 2D, it is easy to uniformly sample points on a curve since the point sequence is naturally ordered. However, it is not easy to consistently sample points on a 3D surface defined by sparse landmarks. Furthermore, in order to build a statistical shape model, correspondence between two shape representations must be established. 3D shape matching techniques can be used for this purpose, but they are often time consuming, error prone, and they need extensive manual interaction.

A heart is composed of four chambers, left ventricle (LV), left atrium (LA), right ventricle (RV), and right atrium (RA). The LV and the LA are connected by the mitral valve (MV), while the RV and the RA are connected by the tricuspid valve (TV). The LV is connected to the aorta via the aortic valve (AV). The main body of the LV is connected to the AV by the left ventricular outflow tract (LVOT). The RV is connected to the pulmonary artery via the pulmonary valve (PV). The right ventricular outflow tract (RVOT) is between the main body of the RV and the PV.

Shape representation is application dependent, and different shape detection methods require different priori information about the shapes, and thus different shape representations. Shape representations can be roughly grouped into two categories of volume-based and surface-based shape representations. Active Shape Models (ASM) and Active Appearance Models (AAM) are examples of models that use shape representations. Since ASM only requires boundary information, surface-based representations are used. Since AAM requires information inside an object, volume-based representations, such as tetrahedrons are used. Embodiments of the present invention utilize a surface mesh representation for heart chamber detection. A mesh can be represented as a graph M={V, F}, where V is an array of vertexes (or mesh points) and F is an array of faces (in our case, triangles). Each vertex is connected to some neighboring vertexes with faces. If at each vertex, the faces connecting to the vertex can be warped to a plane without changing the topology, the mesh is a surface mesh. Otherwise, the mesh is a volume mesh.

The image intensity inside a heart is uniform. For example, the blood pool inside a heart chamber has a consistent intensity. The myocardium muscle has a relatively uniform intensity as well. A large intensity jump can be observed at the boundary between different regions of the heart. Accordingly, the object boundary contains the most information for shape segmentation, and image intensity inside of a region provides little information for boundary delineation. Furthermore, much fewer vertexes are needed to represent a surface mesh, as compared to a volume-based representation. Accordingly, it is much faster to deform a surface mesh during shape detection, and visualization of a surface mesh is easier than a tetrahedral mesh.

Embodiments of the present invention generate a four-chamber heart model that can be used for automatic heart segmentation. An advantageous aspect of the present invention is that the heart model uses an open mesh that explicitly models valves using holes in the mesh. This is more anatomically accurate as compared with a closed surface model mesh. Another advantageous aspect of the present invention is that mesh point correspondence is enforced during mesh editing, such that no time consuming and error prone 3D shape registration is necessary. Another advantageous aspect of the present invention is that important landmarks, such as valves and cusp points on the LV/RV septum, are explicitly represented on the model. These landmarks can be detected reliably to guide the automatic model fitting process. Another advantageous aspect of the present invention is that the heart model is very flexible. Chambers are couple at atrioventricular valves, which are explicitly represented in the model. It is easy to extract each chamber from the whole heart model.

Figure 3:
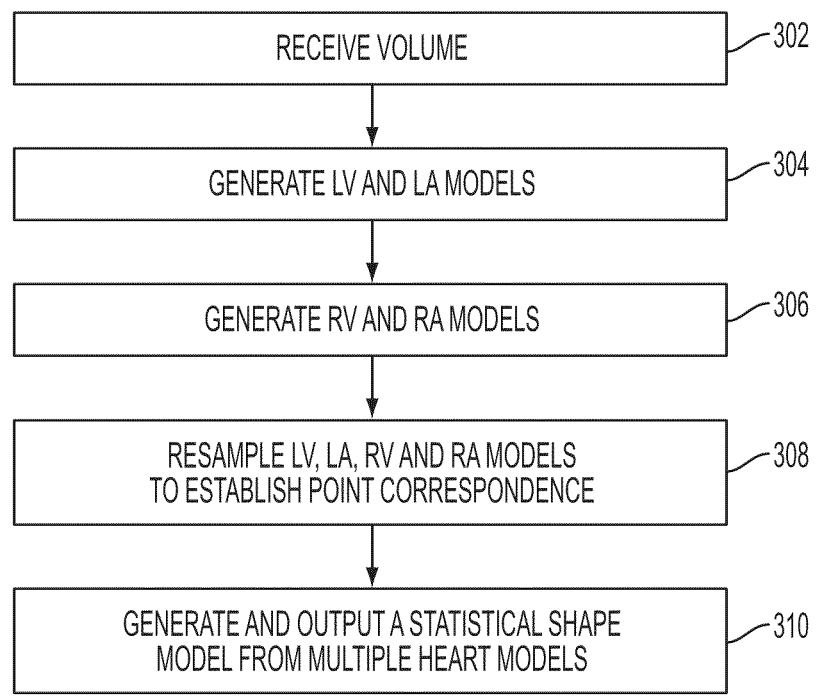
FIG. 3 illustrates a method for generating a statistical four-chamber heart model according to an embodiment of the present invention.

FIG. 3 illustrates a method for generating a statistical four-chamber heart model according to an embodiment of the present invention. At step 302, a 3D volume is received. The volume is a 3D medical image that includes the heart. The volume can be received from a scanning device, such as a computed tomography (CT) scanner. It is also possible that a previously scanned volume that is stored on a computer system or computer readable medium be loaded. As described herein, a CT volume is used in the heart modeling method of FIG. 1, but the present invention is not limited thereto, and other types of 3D volumes can also be used.

At step 304, LV and LA models are generated to represent the LV and LA in the received volume. The LV and LA models can be generated by editing or deforming initial LV and LA meshes. The initial LV and LA meshes can be represented using the mean shape of LV and LA meshes formed based on a set of training volumes. The mitral valve and the aortic valve are determined in the received volume, and then the LV and LA meshes are deformed to fit the volume.

In previous works (mostly 2D based approaches), the LVOT is excluded from LV models. The remaining part of the LV has a simple shape, which is roughly rotation symmetric. With the advancement of 3D medical imaging, having a more anatomically accurate shape model is advantageous. A closed mesh can be used to represent the LV, but a closed mesh excludes the LVOT from the LV in calculating the LV volume and does not model the mitral valve accurately. The mitral valve cusps move during a cardiac cycle. If the mesh follows the movement of the cusps, detection and tracking can be benefited since there are some features (though very weak in most cases) to detect or track. The problem is that the mitral valve cusps are not always visible in a volume. In volumes with bad image quality, these cusps cannot be annotated accurately. The overall results are that in some volumes, the mesh follows the cusps since they are clearly visible, while on other volumes of bad quality, the mesh crosses the mitral valve at an arbitrary position. This will confuse detection and tracking algorithms. Another issue is that under a uniform resampling framework, as described below, the number of points on the mitral valve varies since the size of the mitral valve varies. The mitral valve annulus has characteristic image features and can be detected reliably. Using the previous closed mesh representation, it is knot known which points correspond to the mitral valve annulus. Without this correspondence information, the mitral valve detection cannot be incorporated into the mesh deformation of the LV and LA models.

According to an embodiment of the present invention, the mitral valve annulus is explicitly modeled by opening a hole at a corresponding portion of the LV mesh. This open model can be annotated more consistently during a manual labeling step of a machine learning method for building an automatic heart segmentation system. Accordingly, the model benefits such an automatic heart detection process. A normal mitral valve has a saddle shape. The degree of saddle varies. Some patients with cardiac diseases have a mitral valve with a more flat shape. To facilitate an automatic detection method, a plane is used to approximate the mitral valve in the LV mesh.

Another issue in modeling the LV and the LA is the modeling of both the endocardial and epicardial borders of the LV. These two surfaces converge to a closed contour, which is approximated by a plane in the LV mesh. In a previous system, two separate closed surfaces were used to represent these two surfaces. This is not anatomically accurate. The commissure contour of the endocardial and epicardial borders corresponds to the mitral valve annulus on one side and the aortic valve level (lying at the bottom edge of the Valsalva sinuses) on the other side. Since the angle between these two planes (one for the mitral valve and the other for the commissure plane of the LV endocardial and epicardial borders) is very small, they can be merged into one plane to facilitate the detection method. The combined plane is referred to herein as the mitral valve plane.

Figure 4:
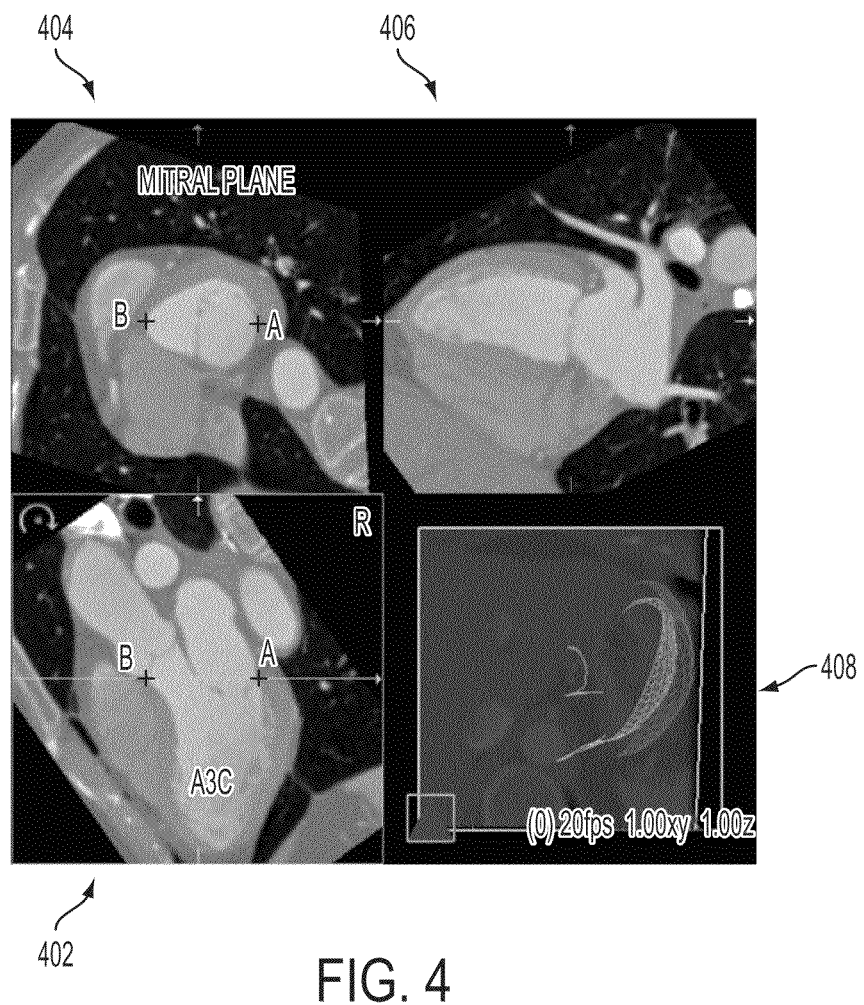
FIG. 4 illustrates determination of a mitral valve plane in a CT volume.
Figure 5:
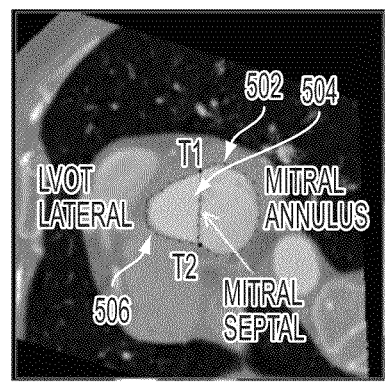
FIG. 5 illustrates control points labeled on the mitral valve plane.

FIG. 4 illustrates determining the mitral valve plane in a CT volume. FIG. 4 shows three orthogonal views (402, 404, and 406) cutting the CT volume. 402 represents the A3C plane, and 404 represents the mitral valve plane. An LV mesh 408 is embedded in the CT volume data. In order to determine the mitral valve plane 404, the A3C plane 402 is selected by manipulating the volume. Two points are determined on the mitral valve plane 404, one at the mitral valve annulus (point A) and the other at the aortic valve level (point B). The plane passing between these two points (A and B) is the mitral valve plane 404. FIG. 5 illustrates control points labeled on the mitral valve plane. Three curves (502, 504, and 506), which are visible in a CT volume with reasonable image quality are annotated on the mitral valve plane, namely, mitral annulus 502, mitral septal 504, and LVOT lateral 506. These three curves (502, 504, and 506) intersect at two points T1 and T2, which can be used as control points in an automatic heart segmentation method.

Figure 6:
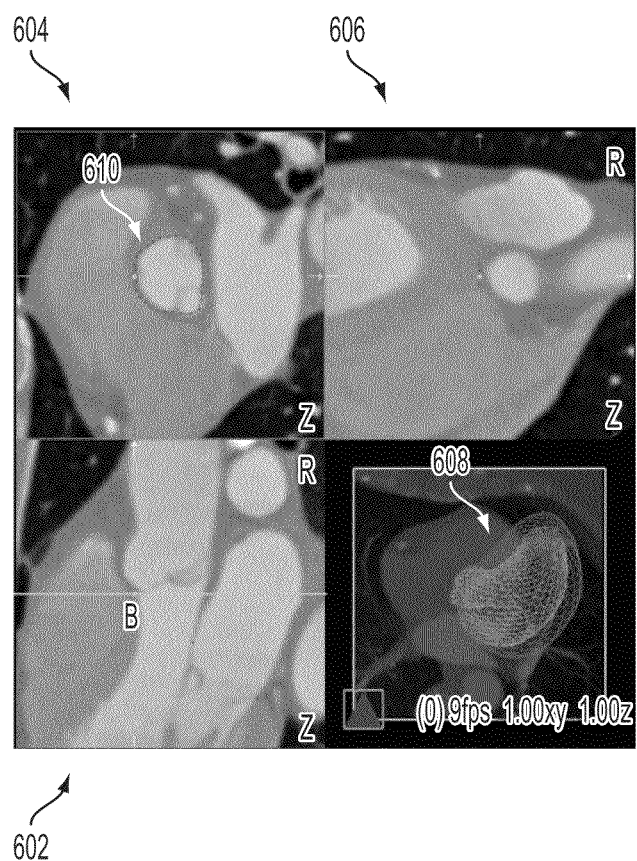
FIG. 6 illustrates annotation of the aortic valve in a CT volume.
Figure 7:
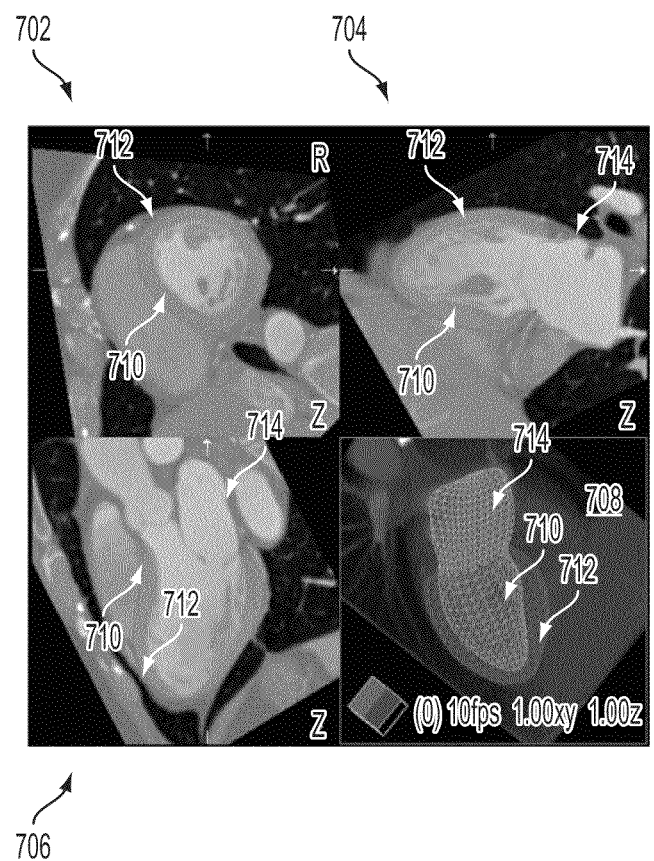
FIG. 7 illustrates left ventricle (LV) and left atrium (LA) meshes generated for a CT volume.

The LV is bounded by the aortic root, which is a protruded structure. Beyond the valve level, there is a mild physiological bulging in the area of the sinuses of Valsalva. The segment between the sinuses of Valsalva and the ascending aorta is called the sinotubular junction. There are three distinctive planes in this anatomy, the valve level, the center of the Valsalva sinuses, and the sinotubular junction. The valve level can be annotated since a point (point B of FIG. 4) at the valve level has already been used to determine the mitral valve plane. This makes the annotation consistent, which makes the detection task easier. Furthermore, the LV volume can be calculated more accurately since the aortic root should be a separate structure and excluded from the LV cavity. FIG. 6 illustrates the annotation of the aortic valve in a CT volume. FIG. 6 shows three orthogonal views (602, 604, and 606) of a CT volume, as well as an LV mesh 608 embedded in the CT volume data. It is possible to annotate the aortic valve using a user input, such as a mouse. As illustrated in FIG. 7, to annotate the aortic valve, the mouse cursor is moved to point B, and the volume is rotated around point B to determine the aortic valve plane 604. The valve boundary 610 can then be annotated as a sequence of control points.

Figure 8:
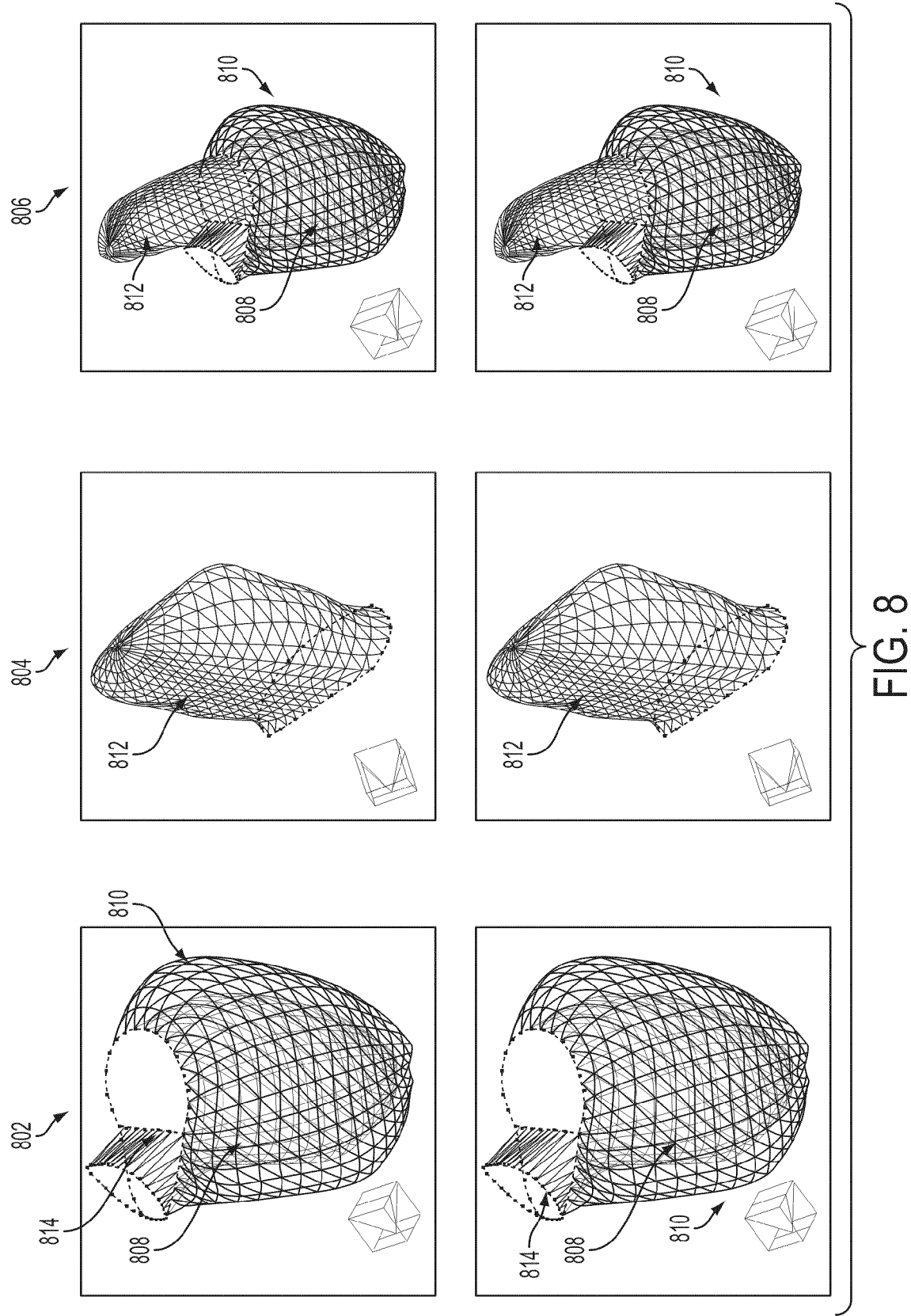
FIG. 8 illustrates LV and LA meshes without volume data.

If a closed LV mesh were used as the initial LV mesh, the annotation tool can automatically generate an open mesh. If there is no initial mesh available, a user can annotate the LV apex, and a cone mesh is generated using the apex as the tip of the cone. The bottom of the cone is generated using the mitral annulus and the mitral septal contours (502 and 504 of FIG. 5). The mesh can be further edited to fit the volume data, and the annotation tool can generate the epicardial mesh by moving the endocardial mesh outwards 10 mm. Minor editing may be required to fit the epicardial mesh to the volume. A degenerated tube can be used to represent the LVOT with one end defined by the aortic valve and the other end defined by the contour defined by the mitral septal and LVOT curves (504 and 506 of FIG. 5). The LA is represented as an open mesh with the hole defined by the mitral septal and mitral annulus curves. The rotation axis based method (described below) is used for resampling during mesh editing of the LV, LVOT, and LA meshes. FIG. 7 illustrates LV and LA meshes generated for a CT volume. FIG. 7 shows three orthogonal views (702, 704, and 706) of a CT volume, as well as a 3D LV and LA mesh (708). As illustrated in FIG. 7, 710 shows the LV endocardial border, 712 shows the LV epicardial border, and 714 shows the LA. FIG. 8 illustrates LV and LA meshes without volume data. FIG. 8 illustrates the LV mesh 802, the LA mesh 804, and the LV plus LA mesh 806. The top row of FIG. 8 shows the mesh triangles, and the bottom row shows the mesh surfaces. As illustrated in FIG. 8, 808 shows the LV endocardial border, 810 shows the LV epicardial border, 812 shows the LA, and 814 shows the LVOT. The LV and LA meshes of FIG. 8 are represented with 514 mesh points and 1056 triangles each. The LVOT mesh 814 is represented with 32 mesh points and 64 triangles.

Returning to FIG. 3, at step 306 RV and RA models are generated to represent the RV and RA in the received volume. The RA and RV models can be generated by editing or deforming initial RV and RA meshes. The initial RV and RA meshes can be represented using the mean shape of RV and RA meshes formed based on a set of training volumes. The U plane, tricuspid valve, and the pulmonary valve are determined in the received volume, and then the RV and RA meshes are deformed to fit the volume.

Figure 9:
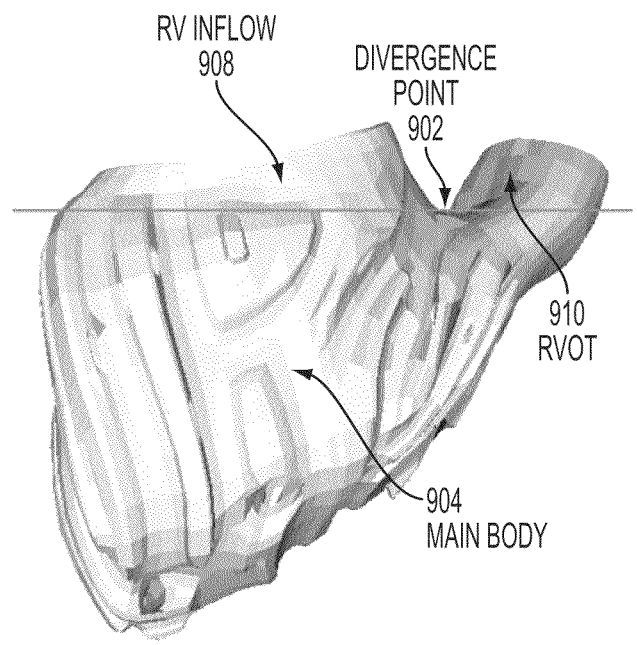
FIG. 9 illustrates dividing the right ventricle (RV) into three portions.

The RV has a more complex shape as compared with the other chambers of the heart. The RV is a truncated ventricle with separate inflow and outflow portions. The shape of the short axis intersection of the RV main body is a crescent. The chamber poorly approximates to any convenient geometric shape. Since, a mesh can be consistently sampled for only a few limited shapes, the RV can be split into multiple pieces, each having a simple shape that can be consistently resampled. The resampling of the RV is described in greater detail below. FIG. 9 illustrates dividing the RV into three portions. As illustrated in FIG. 9, the inflow portion of the RV and the RVOT outflow tract diverge at a divergence point 902. The silhouette of the upper portion of the RV is U-shaped, with the inflow and outflow portions as two arms of the 'U'. The RV can be split into three portions by a plane 904 passing through the divergence point at the bottom of the 'U'. The main body 906 of the RV lies below the cutting plane 904, with the RV inflow tract 908 and the RVOT 910 above the cutting plane 904. The cutting plane 904 is referred to herein as the U-plane.

Figure 10:
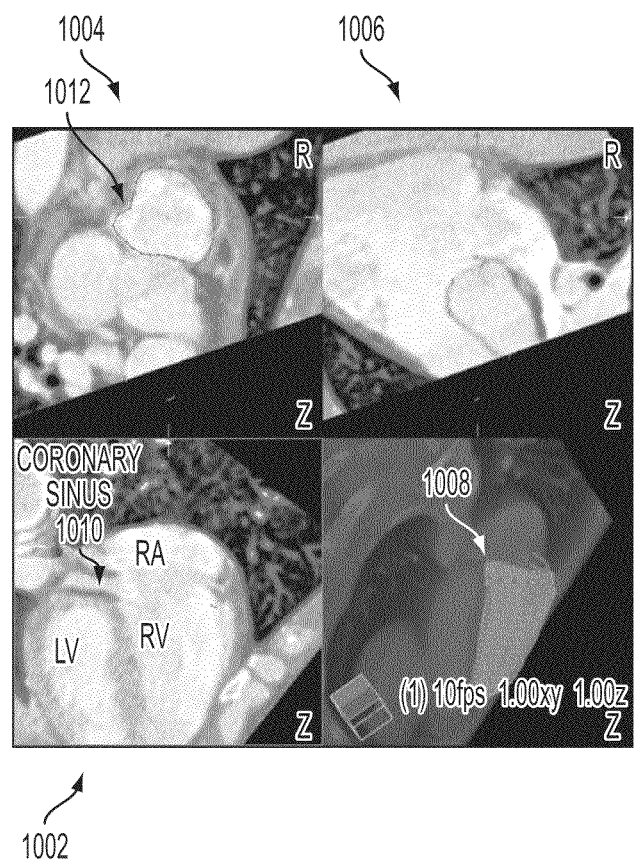
FIG. 10 illustrates determining a tricuspid valve in a CT volume.
Figure 11:
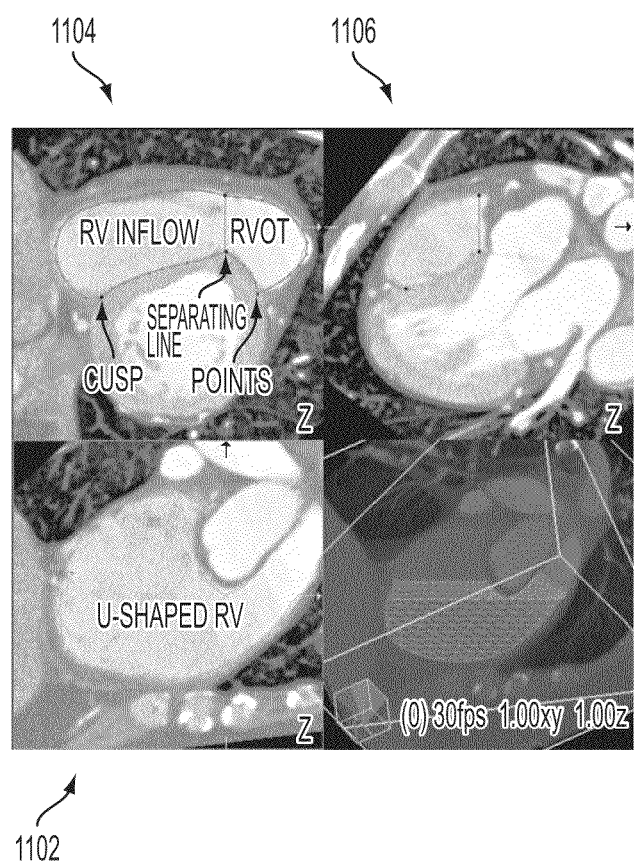
FIG. 11 illustrates annotating control points on a U-plane.

In order to make the annotation consistent across various volumes, the U-plane is selected to be parallel to the tricuspid valve. Accordingly, the tricuspid valve must be detected and annotated in a volume before the U-plane can be annotated. The right side of the heart can have a low contrast in most cardiac CT volumes since a contrast agent can be used to highlight only the left side. It can be difficult to see anatomy in the right side of the heart even after using histogram equalization to increase the contrast. According to an embodiment of the present invention, the coronary sinus can be used to pinpoint the tricuspid valve in the CT volume. FIG. 10 illustrates detecting the tricuspid valve in a CT volume using the coronary sinus. FIG. 10 illustrates three orthogonal views (1002, 1004, and 1006) of a CT volume, as well as an RV mesh 1008 embedded in the volume data. The coronary sinus orifice 1010 lies directly above the tricuspid valve. A plane is used to approximate the tricuspid valve, and the boundary 1012 of the tricuspid valve is annotated. The annotation tool can be used to manipulate the volume in order to determine the U-plane, which is parallel to the tricuspid valve 1012 and passes through the divergence point of the RV inflow portion and the RVOT. FIG. 11 illustrates annotating control points on the U-plane. FIG. 11 shows three orthogonal views (1102, 1004, and 1106) of a CT volume, as well as an RV mesh 1108 embedded in the volume data. In FIG. 11, plane 1104 is the U-plane. As illustrated in FIG. 11, on the U-plane a separating line can be found, where the RV inflow portion and the RVOT diverge. Contours are annotated for the RV inflow portion and the RVOT.

Figure 12:
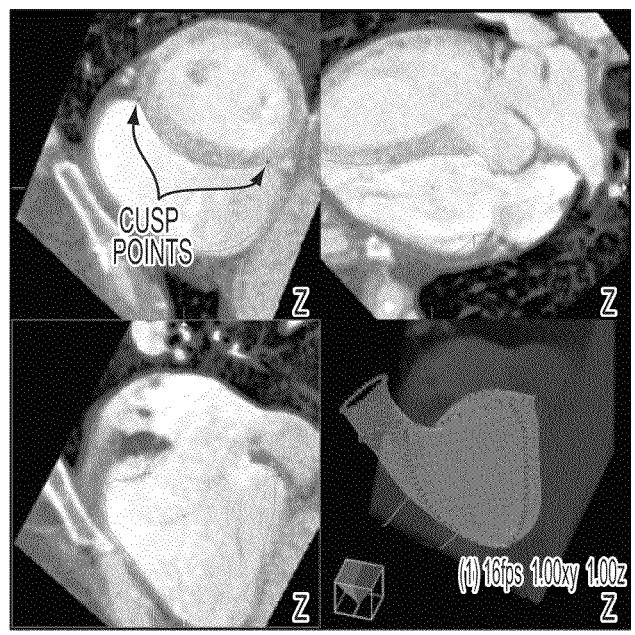
FIG. 12 illustrates annotating cusp points on an LV/RV septal wall.

The shape of the short axis view of the RV main body is a crescent. Two cusp points (shown in FIG. 11) on the intersection are important landmarks, that can be detected reliably using an automatic detection algorithm. These cusps points can be treated specially so that the mesh does not round-off at these locations after imposing smoothing constraints. Accordingly, the cusp points are annotated. FIG. 12 illustrates annotating cusp points on the LV/RV septal wall. The cusp points are annotated starting from the U-plane (FIG. 11), moving down slice by slice until the RV apex is reached. The individually labeled cusp points do not form a smooth curve. As illustrated in FIG. 12, some smoothing may be enforced after the annotation of the cusp points. The cusp point furthest from the U-plane is automatically determined and used as the RV apex.

Figure 13:
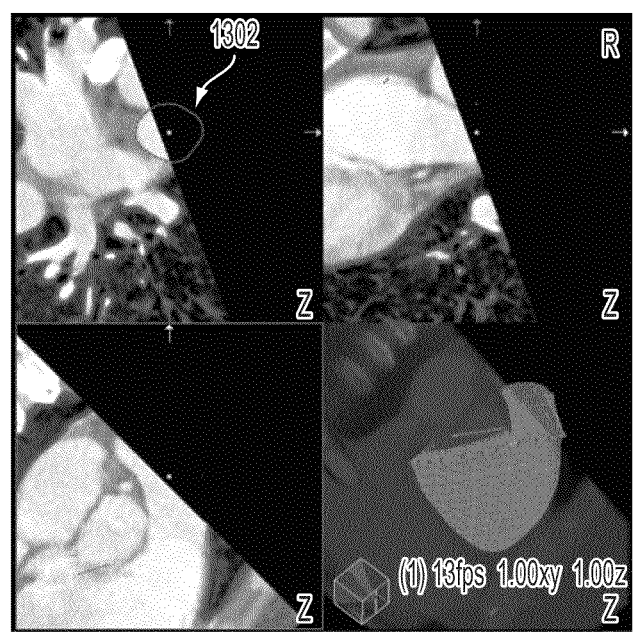
FIG. 13 illustrates annotating a pulmonary valve in a CT volume.
Figure 14C:
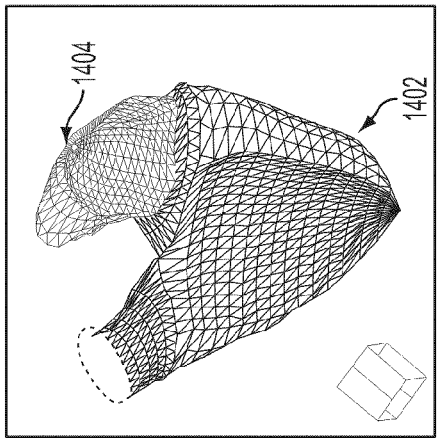
FIG. 14 illustrates RV and RA meshes.
Figure 14F:
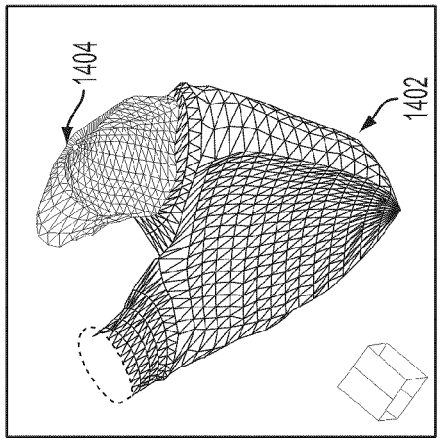
Figure 14B:
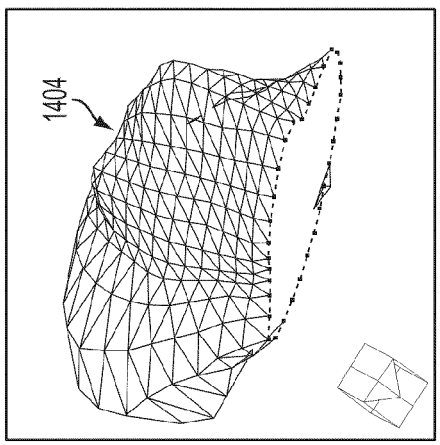
Figure 14E:
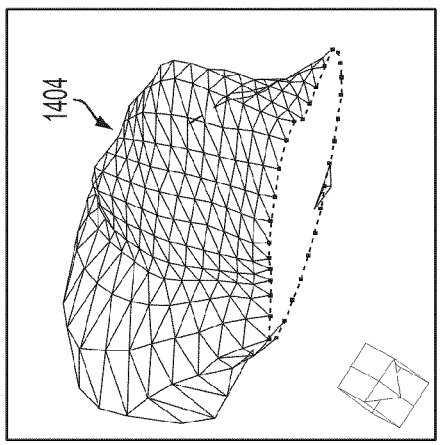
Figure 14A:
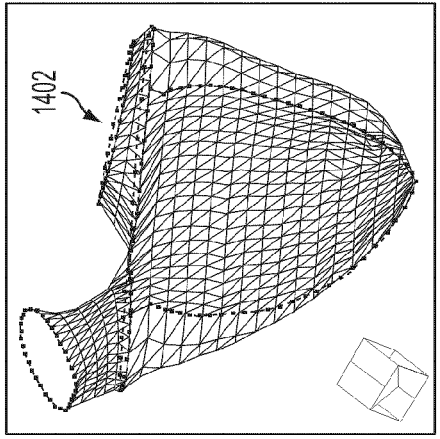
Figure 14D:
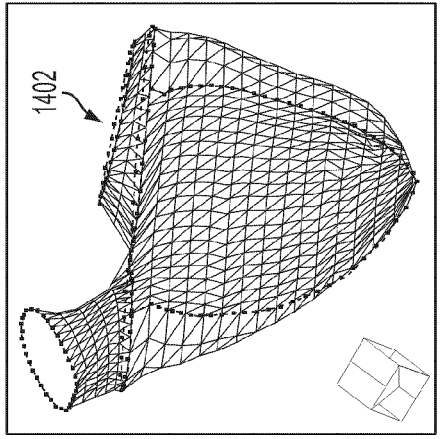

The pulmonary valve can be determined and annotated similarly to the tricuspid valve. To annotate the pulmonary valve, the volume is manipulated to find the pulmonary valve plane and the value is delineated contour using a curve. FIG. 13 illustrates annotating the pulmonary valve in a CT volume. As illustrated in FIG. 13, the boundary 1302 of the pulmonary valve is annotated. For some volumes, the pulmonary valve is mostly located outside of the view of FIG. 13, and the missing part needs to be inferred from the visible part in order to annotate the boundary 1302 of the pulmonary valve.

A slice based method (described below) is used to resample the main body of the RV during mesh editing. The RV inflow portion and the RVOT can be approximated as a tube, and both resampling methods described below can be applied. As describe herein, the slice based resampling method is used for all three portions of the RV, but the present invention is not limited thereto. The RA is represented as an open mesh with a hole defined by the tricuspid valve. FIG. 14 illustrates RV and RA meshes. As illustrated in FIG. 14, 1402 shows the RV mesh and 1404 shows the RA mesh. Images (a) and (d) are the mesh triangles and the mesh surface, respectively, of the RV mesh 1402. Images (b) and (e) are the mesh triangles and the mesh surface, respectively, of the RA mesh 1404. Images (c) and (f) are the mesh triangles and the mesh surface of the RV plus RA mesh. In FIG. 14, the RV is represented with 1568 triangles and the RA is represented with 1056 triangles.

Figure 15:
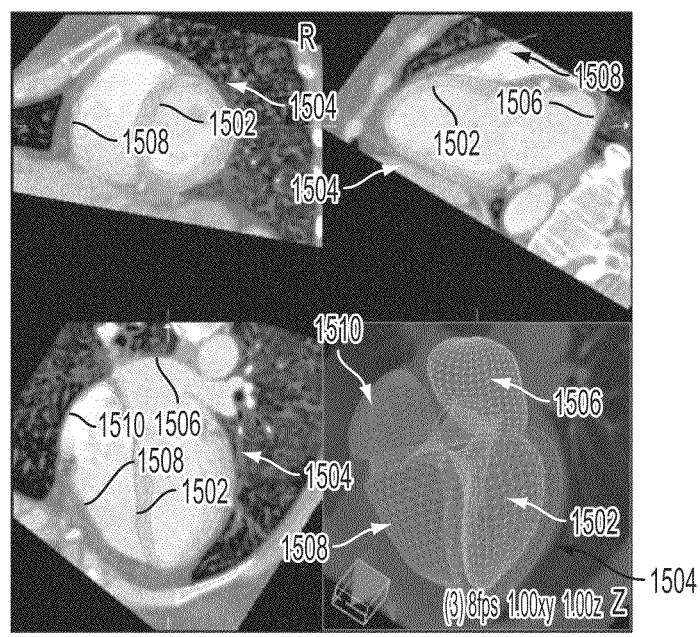
FIG. 15 illustrates a four-chamber model fitted to a CT volume.
Figure 16:
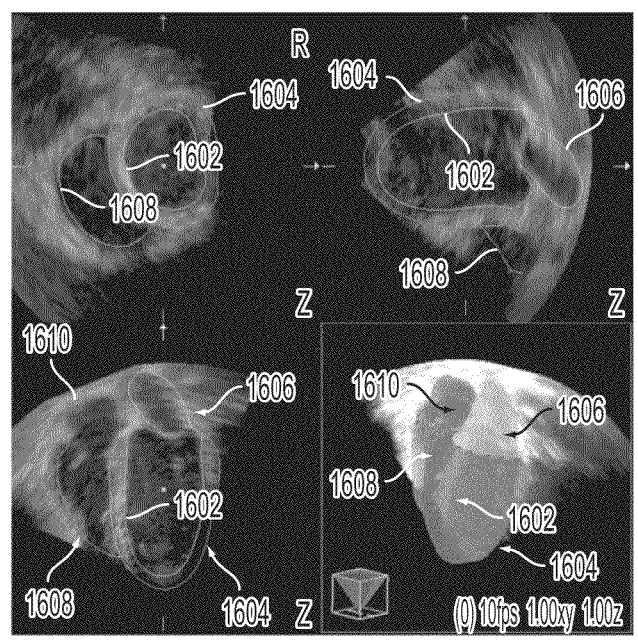
FIG. 16 illustrates a four-chamber model fitted to an ultrasound volume.

The edited LV, LA, RV, and RA meshes may not be smooth. Accordingly, a smoothing technique may be used to achieve a smooth mesh. FIG. 15 illustrates a four-chamber model fitted to a CT volume. As illustrated in FIG. 15, 1502 represents the LV endocardial border, 1504 represents the LV epicardial border, 1506 represents the LA, 1508 represents the RV, and 1510 represents the RA. FIG. 16 illustrates a four-chamber model fitted to an ultrasound volume. As illustrated in FIG. 16, 1602 represents the LV endocardial border, 1604 represents the LV epicardial border, 1606 represents the LA, 1608 represents the RV, and 1610 represents the RA.

Returning to FIG. 3, at step 308, the LV, LA, RV, and RA models are resampled during mesh editing to establish point correspondence between the LV, LA, RV, and RA models generated for the current volume and other models generated for other volumes. During the manual labeling of ground truth, the LV, LA, RV, and RA meshes are edited or deformed to fit the volume data. In this process, point correspondence is lost, and the present invention uses resampling during the mesh editing to establish the point correspondence. According to an embodiment of the present invention, two resampling methods, a rotation axis method and a slice based method, are used to for the this purpose during mesh editing.

Figure 17A:
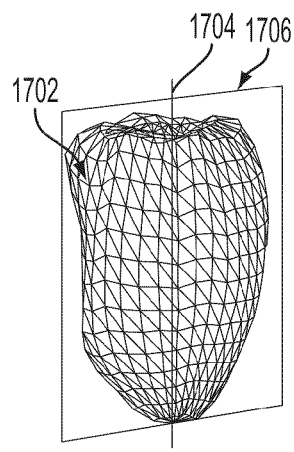
FIG. 17 illustrates a rotation axis resampling method for an LV mesh.
Figure 17B:
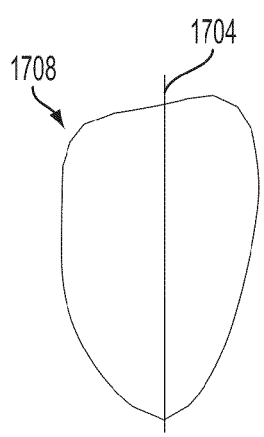
Figure 17C:
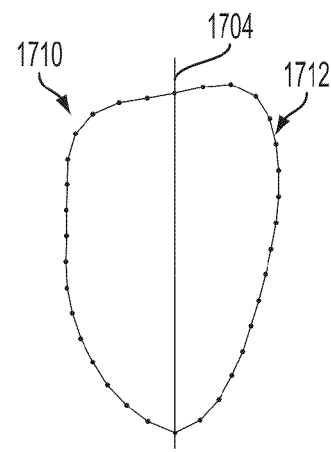

FIG. 17 illustrates the rotation axis resampling method for an LV mesh. The rotation axis method is appropriate for a roughly rotation symmetric shape that has a rotation axis. According to an embodiment of the present invention, the rotation axis resampling method is used to resample the LV, LA, and RA. Image (a) of FIG. 17 illustrates an LV mesh 1702 with its long axis 1704, and a cutting plane 1706 passing through the long axis 1704. The long axis 1704 of the LV mesh 1702 is considered the rotation axis. When a 3D mesh is cut with a cutting plane passing along an axis, it results in a 2D intersection. Image (b) of FIG. 17 shows the 2D intersection 1708 of the mesh 1702 with the cutting plane 1706. As shown in image (c) of FIG. 17, the rotation axis separates the intersection 1708 into two curves 1710 and 1712. Each of the curves 1710 and 1712 can then be resampled independently. The cutting plane 1706 is then rotated around the axis 1704 to get another intersection, which is uniformly resampled. This process is repeated in order to achieve a set of pseudo landmarks. A uniform rotation angle may be used to determine the cutting planes. The rotation axis resampling method is applicable as long as the intersection contains one and only one contour. The correspondence achieved by this approach is perfect under the similarity transformation (e.g., translation, rotation, and scale changes). The correspondence is a reasonable approximation for contraction and expansion motion, which is a major component of the beating of a heart chamber. However, the rotation axis resampling method cannot model twist around the axis.

Figure 18A:
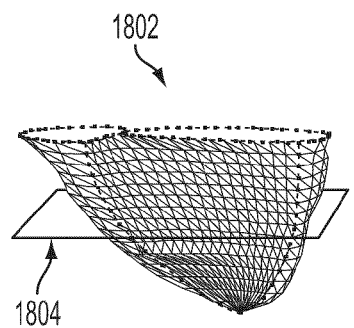
FIG. 18 illustrates a slice based resampling method for an RV mesh.
Figure 18B:
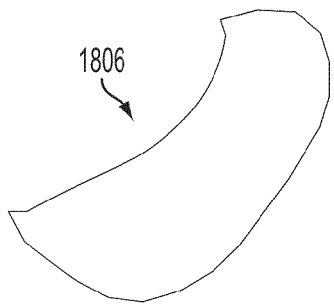
Figure 18C:
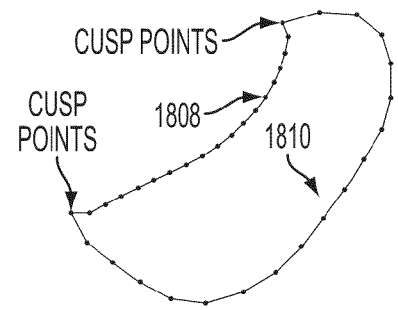

FIG. 18 illustrates the slice based resampling method for an RV mesh. The rotation axis based method is not applicable to the RV. Although the RV has a long axis, the RV is not rotation symmetric around the long axis. The intersection of the RV mesh and a cutting plane passing through the long axis has a complicated shape. The intersection may contain multiple contours since the RV shape is not convex. As illustrated in image (a) of FIG. 18, a cutting plane 1804 that is perpendicular to the long axis of the RV mesh 1802 is used to cut the RV mesh 1802. Image (b) of FIG. 18 shows the intersection 1806 of the RV mesh 1802 with the cutting plane 1804. As long as the intersection 1806 contains one and only one contour, the 2D contours in the intersection can be consistently resampled. Since the 2D intersection 1806 contour of the RV is closed, a starting point must be determined for resampling. For the RV mesh, the shape of the RV short-axis intersection 1806 is a crescent containing two cusp points. As illustrated in image (c) of FIG. 18, the two cusp points split the contour into two curves 1808 and 1810. The two curves 1808 and 1810 are resampled independently. Although the cusp points are used herein to determine a starting point for resampling a 2D intersection, it is to be understood that other methods may also be used to determine a staring point. This method is repeated using a set of parallel planes. The distances between the parallel planes can be uniform. By connecting the resampled points on all intersections, a new resampled mesh is generated.

Returning to FIG. 3, at step 310, from a set of annotated heart mesh models, generated as described above, a statistical shape model of the heart is generated. Since the meshes have built in correspondence from the resampling, procustes analysis and principal component analysis can be applied directly to the meshes to build a statistical shape model. In order to build a statistical shape model multiple heart models are generated, each for an input volume, as described in steps 302-308. A statistical shape model from these multiple heart models can then be generated using the well known Procrustes analysis and principal component analysis. A statistical shape model has two pieces. One is the mean shape, which is the average of multiple shapes. The other contains a set of major components representing the shape variations. The heart model can be output by storing the heart model to a memory, storage, or computer readable medium. The heart model can also be output by displaying the heart model or printing an image of the heart model. The output heart model can be used for further medical image processing. For example, the heart model can be used in an automatic heart segmentation method for segmenting all or a portion of the heart in medical images.

Figure 19:
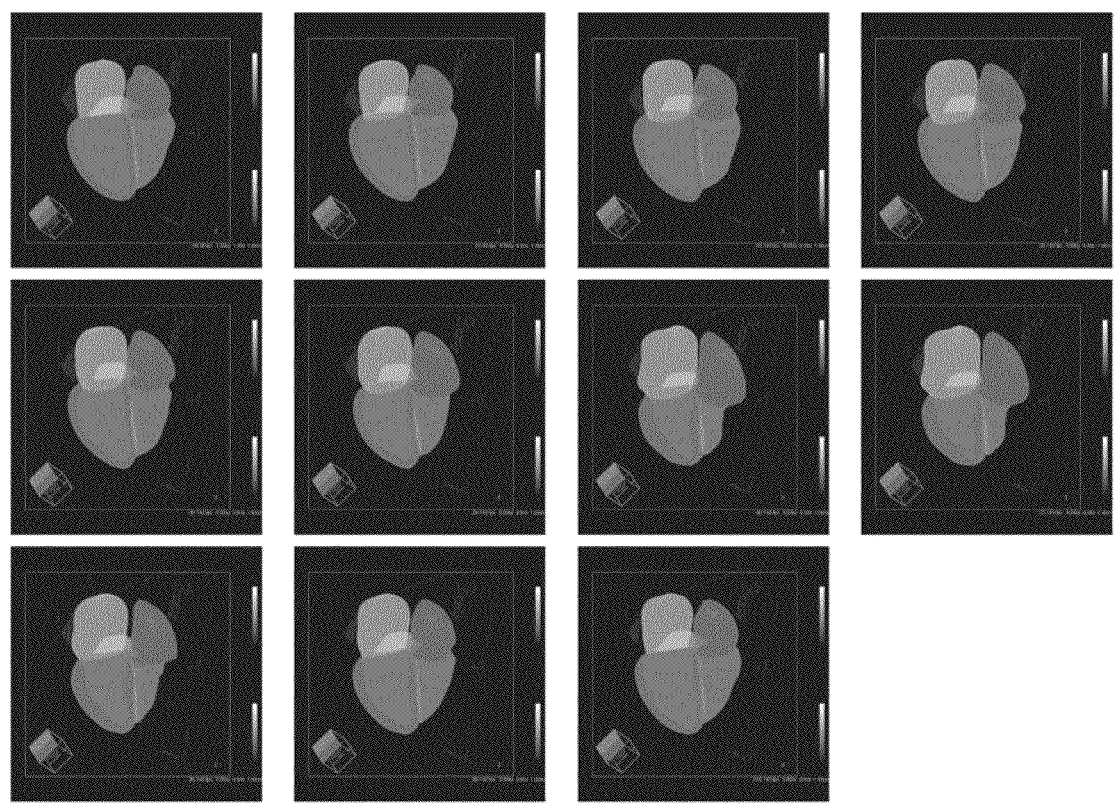
FIG. 19 illustrates four-chamber meshes generated from a dynamic 3D volume sequence.

The method of FIG. 3 is described for a single 3D volume. The method may be similarly applied to dynamic 3D volumes (i.e., moving pictures or video). For a dynamic 3D volume sequence, the above described method can be applied to each volume in the sequence. If the individual meshes are directly combined, the motion pattern is not smooth and coherent. Accordingly, motion smoothing is applied to fine tune the annotations. To reduce artifacts introduced in motion smoothing, an end-diastolic (ED) frame and an end-systolic (ES) frame can be determined based on LV volumes. These two frames are fixed and the other frames are smoothed. Since the point correspondence is enforced during mesh editing, motion smoothing can be applied to each mesh point independently. The smoothed point position is the weighted average of the current, previous, and next frames. FIG. 19 illustrates four-chamber meshes generated from a dynamic 3D sequence with 11 frames.

Figure 20:
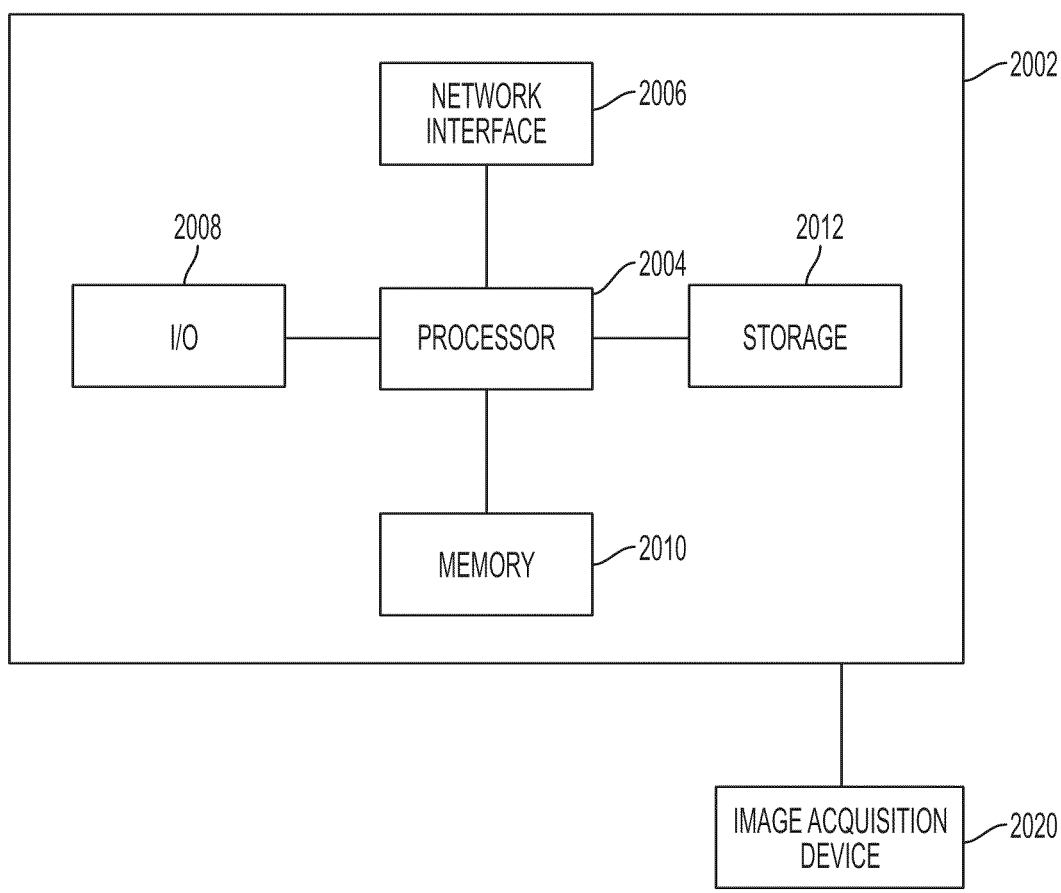
FIG. 20 is a high level block diagram of a computer capable of implementing the present invention.

The above-described methods for generating a four-chamber heart model may be implemented on a computer using well-known computer processors, memory units, storage devices, computer software, and other components. A high level block diagram of such a computer is illustrated in FIG. 20. Computer 2002 contains a processor 2004 which controls the overall operation of the computer 2002 by executing computer program instructions which define such operation. The computer program instructions may be stored in a storage device 2012 (e.g., magnetic disk) and loaded into memory 2010 when execution of the computer program instructions is desired. Thus, the steps of the method of FIG. 3 may be defined by the computer program instructions stored in the memory 2010 and/or storage 2012 and controlled by the processor 2004 executing the computer program instructions. For example, the processor 2004 can execute computer program instructions for detecting anatomical landmarks in the heart, annotating volumes, editing or deforming meshes, resampling the meshes, etc. Furthermore, models (meshes) generated by the above described methods can be stored in the memory 2010 and/or storage 2012. An image acquisition device 2020, such as a CT scanning device, can be connected to the computer 2002 to input the 3D volumes to the computer 2002. It is possible to implement the image acquisition device 2020 and the computer 2002 as one device. It is also possible that the image acquisition device 2020 and the computer 2002 communicate wirelessly through a network. The computer 2002 also includes one or more network interfaces 2006 for communicating with other devices via a network. The computer 2002 also includes other input/output devices 2008 that enable user interaction with the computer 2002 (e.g., display, keyboard, mouse, speakers, buttons, etc.). Such input/output devices 2008 may be used in conjunction with a set of computer programs as an annotation tool to annotate volumes received from the image acquisition device 2020. One skilled in the art will recognize that an implementation of an actual computer could contain other components as well, and that FIG. 20 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for generating a four-chamber heart model, comprising:
    receiving a 3D volume;
    generating a left ventricle (LV) mesh and a left atrium (LA) mesh based on said 3D volume;
    generating a right ventricle (RV) mesh and a right atrium (RA) mesh based on said 3D volume;
    resampling each of said LV, LA, RV, and RA meshes to establish point correspondence between said LV, LA, RV, and RA meshes and meshes generated based on other 3D volumes; and
    generating a statistical four-chamber heart shape model based on said LV, LA, RV, and RA meshes displaying the statistical four chamber heart shape model.

2. The method of claim 1, wherein:
    said step of generating an LV mesh and an LA mesh comprises editing an initial LV mesh and an initial LA mesh based on said 3D volume;
    said step of generating an RV mesh and an RA mesh comprises editing an initial RV mesh and an initial RA mesh based on said 3D volume; and
    said step of resampling each of said LV, LA, RV, and RA meshes comprises resampling each of said LV, LA, RV, and RA meshes during the editing of the each of said initial LV, LA, RV, and RA meshes.

3. The method of claim 1, wherein said step of resampling of each of said LV, LA RV, and RA meshes comprises:
    resampling said LV, LA, and RA meshes using rotation axis based resampling; and
    resampling said RV mesh using slice based resampling.

4. The method of claim 3, wherein said step of resampling said LV, LA, and RA meshes using rotation axis based resampling comprises for each mesh:
    defining a rotation axis along a long axis of the mesh;
    cutting the mesh with a plane that passing through the rotation axis to generate a 2D contour at the intersection the mesh and the plane, wherein the rotation axis divides the 2D contour into two curves;
    uniformly resampling the two curves of the 2D contour independently from one another;
    repeatedly rotating the plane around the rotation axis to define a series of 2D contours, the rotation axis dividing each 2D contour into two curves; and
    uniformly resampling the two curves of each 2D contour independently from one another.

5. The method of claim 3, wherein said step of resampling said RV mesh using slice based resampling comprises:
    cutting the RV mesh by a set of parallel planes, each plane perpendicular to a long axis of the RV mesh, to generate a series of 2D slices each having a single contour;
    dividing the contour of each slice into two curves that meet at a pair of cusp points; and
    uniformly resampling the two curves of each slice independently from one another.

6. The method of claim 1, wherein said step of generating a left ventricle (LV) mesh and a left atrium (LA) mesh based on said 3D volume comprises:
    detecting and annotating a mitral valve in said 3D volume;
    detecting and annotating an aortic valve in said 3D volume; and
    deforming an initial LV mesh and an initial LA mesh based on the mitral valve and the aortic valve in said 3D volume.

7. The method of claim 1, wherein said step of generating a right ventricle (RV) mesh and a right atrium (RA) mesh based on said 3D volume comprises:
    detecting and annotating a plane in said 3D volume that divides the RV into an RV main body, an RV inflow tract, and an RV outflow tract;
    detecting and annotating a tricuspid valve in said 3D volume;
    detecting and annotating a pulmonary valve in said 3D volume; and
    deforming an initial RV mesh and an initial RA mesh based on said plane, said tricuspid valve, and said pulmonary valve in said 3D volume.

8. The method of claim 1, wherein said LV, LA, RV, and RA meshes are open meshes with holes representing valves.

9. The method of claim 1, wherein said LV mesh models endocardial and epicardial borders of the LV.

10. An apparatus for generating a four-chamber heart model, comprising:
    a processor; and
    a memory storing computer program instructions, which when executed by the processor cause the processor to perform operations comprising:
    receiving a 3D volume;
    generating a left ventricle (LV) mesh and a left atrium (LA) mesh based on said 3D volume;
    generating a right ventricle (RV) mesh and a right atrium (RA) mesh based on said 3D volume;
    resampling each of said LV, LA, RV, and RA meshes to establish point correspondence between said LV, LA, RV, and RA meshes and meshes generated based on other 3D volumes; and
    generating a statistical four-chamber heart shape model based on said LV, LA, RV, and RA meshes displaying the statistical four chamber heart shape model.

11. The apparatus of claim 10, wherein:
    said operation of generating an LV mesh and an LA mesh comprises means for editing an initial LV mesh and an initial LA mesh based on said 3D volume;
    said operation of generating an RV mesh and an RA mesh comprises means for editing an initial RV mesh and an initial RA mesh based on said 3D volume; and
    said operation of resampling each of said LV, LA, RV, and RA meshes comprises means for resampling each of said LV, LA, RV, and RA meshes during the editing of the each of said initial LV, LA, RV, and RA meshes.

12. The apparatus of claim 10, wherein resampling of each of said LV, LA, RV, and RA meshes comprises:
resampling said LV, LA, and RA meshes using rotation axis based resampling; and
resampling said RV mesh using slice based resampling.

13. The apparatus of claim 12, wherein resampling said LV, LA, and RA meshes using rotation axis based resampling comprises for each mesh:
defining a rotation axis along a long axis of the mesh;
cutting the mesh with a plane that passing through the rotation axis to generate a 2D contour at the intersection the mesh and the plane, wherein the rotation axis divides the 2D contour into two curves; and
uniformly resampling the two curves of the 2D contour independently from one another.

14. The apparatus of claim 12, wherein resampling said RV mesh using slice based resampling comprises:
cutting the RV mesh by a set of parallel planes, each plane perpendicular to a long axis of the RV mesh, to generate a series of 2D slices each having a single contour;
dividing the contour of each slice into two curves that meet at a pair of cusp points; and
uniformly resampling the two curves of each slice independently from one another.

15. The apparatus of claim 10, wherein generating a left ventricle (LV) mesh and a left atrium (LA) mesh based on said 3D volume comprises:
detecting and annotating a mitral valve in said 3D volume;
detecting and annotating an aortic valve in said 3D volume; and
deforming an initial LV mesh and an initial LA mesh based on the mitral valve and the aortic valve in said 3D volume.

16. The apparatus of claim 10, wherein generating a right ventricle (RV) mesh and a right atrium (RA) mesh based on said 3D volume comprises:
detecting and annotating a plane in said 3D volume that divides the RV into an RV main body, an RV inflow tract, and an RV outflow tract;
detecting and annotating a tricuspid valve in said 3D volume;
detecting and annotating a pulmonary valve in said 3D volume; and
deforming an initial RV mesh and an initial RA mesh based on said plane, said tricuspid valve, and said pulmonary valve in said 3D volume.

17. The apparatus of claim 10, wherein said LV, LA, RV, and RA meshes are open meshes with holes representing valves.

18. The apparatus of claim 10, wherein said LV mesh models endocardial and epicardial borders of the LV.

19. A non-transitory computer readable medium encoded with computer executable instructions for generating a four-chamber heart model, the computer executable instructions defining steps comprising:
receiving a 3D volume;
generating a left ventricle (LV) mesh and a left atrium (LA) mesh based on said 3D volume;
generating a right ventricle (RV) mesh and a right atrium (RA) mesh based on said 3D volume;
resampling each of said LV, LA, RV, and RA meshes to establish point correspondence between said LV, LA, RV, and RA meshes and meshes generated based on other 3D volumes; and
generating a statistical four-chamber heart shape model based on said LV, LA, RV, and RA meshes displaying the statistical four chamber heart shape model.

20. The non-transitory computer readable medium of claim 19, wherein:
the computer executable instructions defining the step of generating an LV mesh and an LA mesh comprise computer executable instructions defining the step of editing an initial LV mesh and an initial LA mesh based on said 3D volume;
the computer executable instructions defining the step of generating an RV mesh and an RA mesh comprise computer executable instructions defining the step of editing an initial RV mesh and an initial RA mesh based on said 3D volume; and
the computer executable instructions defining the step of resampling each of said LV, LA, RV, and RA meshes comprise computer executable instructions defining the step of resampling each of said LV, LA, RV, and RA meshes during the editing of the each of said initial LV, LA, RV, and RA meshes.

21. The non-transitory computer readable medium of claim 19, wherein the computer executable instructions defining the step of resampling of each of said LV, LA RV, and RA meshes comprise computer executable instructions defining the steps of:
resampling said LV, LA, and RA meshes using rotation axis based resampling; and
resampling said RV mesh using slice based resampling.

22. The non-transitory computer readable medium of claim 21, wherein the computer executable instructions defining the step of resampling said LV, LA, and RA meshes using rotation axis based resampling comprise for each mesh, computer executable instructions defining the steps of:
defining a rotation axis along a long axis of the mesh;
cutting the mesh with a plane that passing through the rotation axis to generate a 2D contour at the intersection the mesh and the plane, wherein the rotation axis divides the 2D contour into two curves;
uniformly resampling the two curves of the 2D contour independently from one another;
repeatedly rotating the plane around the rotation axis to define a series of 2D contours, the rotation axis dividing each 2D contour into two curves; and
uniformly resampling the two curves of each 2D contour independently from one another.

23. The non-transitory computer readable medium of claim 21, wherein the computer executable instructions defining the step of resampling said RV mesh using slice based resampling comprise computer executable instructions defining the steps of:
cutting the RV mesh by a set of parallel planes, each plane perpendicular to a long axis of the RV mesh, to generate a series of 2D slices each having a single contour;
dividing the contour of each slice into two curves that meet at a pair of cusp points; and
uniformly resampling the two curves of each slice independently from one another.

24. The non-transitory computer readable medium of claim 19, wherein the computer executable instructions defining the step of generating a left ventricle (LV) mesh and a left atrium (LA) mesh based on said 3D volume comprise computer executable instructions defining the steps of:
detecting and annotating a mitral valve in said 3D volume;
detecting and annotating an aortic valve in said 3D volume; and deforming an initial LV mesh and an initial LA mesh based on the mitral valve and the aortic valve in said 3D volume.

25. The non-transitory computer readable medium of claim 19, wherein the computer executable instructions defining the step of generating a right ventricle (RV) mesh and a right atrium (RA) mesh based on said 3D volume comprise computer executable instructions defining the steps of:

detecting and annotating a plane in said 3D volume that divides the RV into an RV main body, an RV inflow tract, and an RV outflow tract;
  detecting and annotating a tricuspid valve in said 3D volume;
  detecting and annotating a pulmonary valve in said 3D volume; and
  deforming an initial RV mesh and an initial RA mesh based on said plane, said tricuspid valve, and said pulmonary valve in said 3D volume.

* * * * *